United States Patent
Ci (10) Patent No.: US 10,893,689 B2
(45) Date of Patent: Jan. 19, 2021

(54) SOLID BEVERAGE FOR CONDITIONING BLOOD STASIS CONSTITUTION AND METHOD FOR PRODUCING THE SAME

(71) Applicant: Zhonghua Ci, Beijing (CN)

(72) Inventor: Zhonghua Ci, Beijing (CN)

( * ) Notice: Subject to any disclaimer, the term of this patent is extended or adjusted under 35 U.S.C. 154(b) by 389 days.

(21) Appl. No.: 15/874,319

(22) Filed: Jan. 18, 2018

(65) Prior Publication Data

US 2019/0159484 A1 May 30, 2019

(30) Foreign Application Priority Data

Nov. 30, 2017 (CN) .......................... 2017 1 1242628

(51) Int. Cl.

| | |
|---|---|
| *A23L 2/39* | (2006.01) |
| *A61K 36/16* | (2006.01) |
| *A61K 36/736* | (2006.01) |
| *A61K 36/346* | (2006.01) |
| *A61K 36/54* | (2006.01) |
| *A61K 36/488* | (2006.01) |
| *A61K 36/734* | (2006.01) |

(52) U.S. Cl.
CPC ................ *A23L 2/39* (2013.01); *A61K 36/16* (2013.01); *A61K 36/346* (2013.01); *A61K 36/488* (2013.01); *A61K 36/54* (2013.01); *A61K 36/734* (2013.01); *A61K 36/736* (2013.01); *A23V 2002/00* (2013.01)

(58) Field of Classification Search
None
See application file for complete search history.

(56) References Cited

FOREIGN PATENT DOCUMENTS

| CN | 104256612 A | 1/2015 |
| CN | 107048142 A | 8/2017 |
| CN | 107050304 A | 8/2017 |

OTHER PUBLICATIONS

CN104305180A translation (retrieved from Espacenet) (Year: 2015).*
Guo Yong, et al: "Applicaton of Enzyme in Food Industry"; Beijing; China Light Industry Press, 1996.11 ISBN 7-5019-1948-8; pp. 3.
Pinghe Source; Chinese Medicine Constititution Conditioning Technology LEading Brand; Peace Source; printed Sep. 6, 2020; pp. 1.

* cited by examiner

*Primary Examiner* — Michael Barker
(74) *Attorney, Agent, or Firm* — Cantor Colburn LLP (57) ABSTRACT

The present application discloses a solid beverage for conditioning blood stasis constitution. The solid beverage comprises the following components in parts by weight: 21-55 parts of hawthorn, 9-33 parts of peach seed, 9-33 parts of gingko, 5-21 parts of *Platycodon grandiflorus*, 9-33 parts of dried tangerine peel, 0.5-4 parts of cinnamon, 9-33 parts of the root of kudzu vine, 2-21 parts of *Dahurian angelica*, 10-29 parts of dextrin, 7-25 parts of maltodextrin, 8-26 parts of soluble starch and 0.05-0.2 parts of aspartame. The solid beverage of the present application is simple and convenient to prepare, the raw materials used are all medicinal materials with dual-purpose of drug and food, and the auxiliary materials used also meet the national standard GB2760-2011 (the National Food Safety Standard for Food Additive Use). Thus, the solid beverage is safe to consume and good in taste, and has certain effects on the improvement of blood stasis constitution, and the production process thereof is suitable for industrial mass production.

10 Claims, 2 Drawing Sheets

SOLID BEVERAGE FOR CONDITIONING BLOOD STASIS CONSTITUTION AND METHOD FOR PRODUCING THE SAME

TECHNICAL FIELD

The present invention relates to the field of health foods, and particularly to a solid beverage for conditioning blood stasis constitution and a method for producing the same.

BACKGROUND

In *Classification and Determination of Constitution in Traditional Chinese Medicine*, the China Association of Chinese Medicine classifies body constitutions of the human body into nine types, i.e., yin-yang harmony constitution, yang deficiency constitution, yin deficiency constitution, qi deficiency constitution, phlegm-dampness constitution, damp-heat constitution, qi stagnation constitution, blood stasis constitution and allergic constitution, most of which are sub-healthy states.

The main symptom of blood stasis constitution is sluggish circulation of the blood, which is mainly caused by prolonged depression of emotion and volition, long-term residence in cold places, dysfunction of internal organs, and mainly occurs in relatively thin people. The clinical manifestation is as follows: when blood stagnates at a certain place of the internal organs or of main and collateral channels, a pain is incurred at a fixed place, and the pain cannot be relieved with warmness, and even leads to the formation of a lump. For people with such constitution, some have senile plaques even when they are not old enough, and some often suffer from a pain in a certain place, for example, the female easily have dysmenorrhea in the physiological period, the male usually have bruises on their bodies, and the pain in the body worsens at night, etc.

Such sub-healthy constitution as blood stasis constitution belongs to chronic diseases and has a relatively long disease course, and requires a long-term medication and gradual conditioning, in order to achieve the effects of consolidating the vital essence and strengthening the origin, and strengthening the body resistance to eliminate pathogenic factors. The dosage forms commonly used in the traditional Chinese medicine are decoctions and Chinese patent medicine such as pills and the like. Decoctions usually have relatively good efficacy, but the administration thereof is complicated, and the taste thereof is poor, if the decoctions need to be administered for a long time, it is difficult for a patient to keep taking the decoctions. Moreover, the efficacy of the pills is relatively poor.

Food is the best product for human beings to prevent diseases and keep healthy. The theory that "medicine and food share a common origin" is one of the most valuable contributions made by the original Chinese medicine to human beings. It is described in the *Rites of Zhou•Offices of the Heaven•Medicine* that "diseases are treated with the five flavors, the five grains and the five medicines", which demonstrates the physical health-care functions of food. The method of regulating body functions using the characteristics of food so as to obtain health or prevent or treat diseases is called dietary therapy. However, "therapy" is inferior to "nourishing", and food nourishing is an approach to increase resistance against diseases and enhance immunity by eating tonic food according to food nutrition in combination with the body conditions, so as to strengthen the body and prolong the life. It is described in *Prescriptions Worth a Thousand Gold* that "a physician should first know the cause of a disease to know why the disease is developed and treat the disease with food materials. Only when food materials are unable to treat the disease, can drugs be used." Thus, dietary therapy was not only the basic therapeutic approach of the physicians at that time, but also an important criterion for determining whether a physician was a great physician.

It is mentioned in the *Inner Canon of the Yellow Emperor* that "the superior physician prevents illness, the mediocre physician attends to impending illness, and the inferior physician treats actual illness", wherein the phrase "prevent illness" means taking corresponding measures to prevent the occurrence and development of diseases. The body constitution determines the health of people and determines the susceptibility to diseases. Faced with the situations that there are various diseases in modern society, the age of onset becomes lower and lower and there are more and more sub-healthy people, dietary therapy gets more and more popular with the consumers due to its advantages of being healthy and natural, and with respect to the diseases that are easy to develop, it is of great significance to develop a food product that has the functions of life nourishing and health protection, has a good taste and conditions the blood stasis constitution, by using modern scientific technologies and methods and the theory that "medicine and food share a common origin", referring to the precious Chinese traditional life nourishing experience in combination with good accumulation of the traditional Chinese medicine on the aspect of conditioning blood stasis constitution.

DISCLOSURE OF THE INVENTION

The main object of the present invention is to provide a life nourishing and health protecting food product for conditioning blood stasis constitution.

In order to achieve the above object, according to one aspect of the present invention, there is provided a solid beverage for conditioning blood stasis constitution.

The solid beverage for conditioning blood stasis constitution according to the present invention comprises the following components in parts by weight: 21-55 parts of hawthorn, 9-33 parts of peach seed, 9-33 parts of gingko, 5-21 parts of *Platycodon grandiflorus*, 9-33 parts of dried tangerine peel, 0.5-4 parts of cinnamon, 9-33 parts of the root of kudzu vine, 2-21 parts of *Dahurian angelica*, 10-29 parts of dextrin, 7-25 parts of maltodextrin, 8-26 parts of soluble starch and 0.05-0.2 parts of aspartame.

Further, the solid beverage for conditioning blood stasis constitution according to the present invention comprises the following components in parts by weight: 30-44 parts of hawthorn, 15-23 parts of peach seed, 17-28 parts of gingko, 9-17 parts of *Platycodon grandiflorus*, 15-28 parts of dried tangerine peel, 1-3 parts of cinnamon, 14-23 parts of the root of kudzu vine, 8-17 parts of *Dahurian angelica*, 19-24 parts of dextrin, 10-22 parts of maltodextrin, 13-22 parts of soluble starch and 0.1-0.15 parts of aspartame.

Further, the solid beverage for conditioning blood stasis constitution according to the present invention comprises the following components in parts by weight: 40 parts of hawthorn, 20 parts of peach seed, 20 parts of gingko, 12 parts of *Platycodon grandiflorus*, 20 parts of dried tangerine peel, 2 parts of cinnamon, 20 parts of the root of kudzu vine, 12 parts of *Dahurian angelica*, 19 parts of dextrin, 15 parts of maltodextrin, 15 parts of soluble starch and 0.1 parts of aspartame.

In order to achieve the above object, according to another aspect of the present invention, there is provided a method for producing a solid beverage for conditioning blood stasis constitution.

The method for producing a solid beverage for conditioning blood stasis constitution according to the present invention comprises the steps of:

(1) preparation of raw materials: subjecting peach seed, hawthorn, the root of kudzu vine, gingko, dried tangerine peel, *Dahurian angelica, Platycodon grandiflorus* and cinnamon to impurity removal, cleansing, cutting and pulverization, and then mixing them for later use;

(2) decoction: decocting the mixture resulting from step (1) with water twice to obtain a traditional Chinese medicine liquid;

(3) concentration: pumping the traditional Chinese medicine liquid prepared in step (2) into an inspissator through a pipe to concentrate the same into thick paste; and (4) wet granulation: mixing and stirring dextrin, maltodextrin, soluble starch and aspartame to obtain a mixture adjuvant, adding the thick paste prepared in step (3) to the mixture adjuvant, and stirring the same for granulation.

Further, the two-time decoction process in step (2) is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction.

Further, the temperature for the concentration in step (3) is 70-80° C., and the relative density of the prepared thick paste is 1.2-1.5 at the temperature of 50° C.

Further, the wet granulation in step (4) comprises the steps of:

(4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving;

(4.3) drying: putting the sieved particles prepared from step (4.2) into a boiling dryer for drying; and (4.4) secondary sieving: carrying out secondary sieving by using a wig-wag machine.

Further, the sieve for the primary sieving is a 12-mesh sieve, and the sieve for the secondary sieving is a 10-mesh sieve.

Further, in the drying process in step (4.3), the temperature of the materials is controlled to be 70-80° C., and the moisture of the final materials is controlled to be 5% or less.

Further, after the secondary sieving, the method further comprises a particle selecting step to select particles of 10-60 meshes.

The solid beverage of the present invention is simple and convenient to prepare, the raw materials used are all medicinal materials with dual-purpose of drug and food, and the auxiliary materials used also meet the national standard GB2760-2011 (the National Food Safety Standard for Food Additive Use). Thus, the solid beverage is safe to consume and good in taste, a long-term consumption of the solid beverage has certain effects on the improvement of blood stasis constitution, and the production process thereof is suitable for industrial mass production.

BRIEF DESCRIPTION OF DRAWINGS

The accompanying drawings, which constitute a part of the present application, are used to provide a further understanding of the present invention, so that other features, objects and advantages of the present application become more obvious. The illustrative drawings for embodiments of the present invention and the description thereof are used to explain the present invention, rather than constitute an improper limitation on the present invention. In the drawings.

DETAILED DESCRIPTION OF EMBODIMENTS

In order to enable a person skilled in the art to better understand the solutions of the present application, the technical solutions of the embodiments of the present invention will be described clearly and completely below with reference to the drawings of the embodiments of the present application. Apparently, the embodiments described are some of the embodiments of the present application, rather than all of the embodiments. All the other embodiments that are obtained by a person skilled in the art without inventive effort on the basis of the embodiments of the present application shall be covered by the protection scope of the present application.

In addition, the term "comprise" and any variant thereof are intended to cover non-exclusive inclusion, for example, a product comprising a series of raw materials or a method comprising a series of steps is not necessarily limited to the raw materials or the steps listed clearly, but can include other steps or raw materials that are not clearly listed or are inherent to the method and product.

It should be noted that the embodiments of the present application and the features of the embodiments can be combined with each other if there is no conflict. The present application will be described in detail below with reference to the accompanying drawings and embodiments.

The main object of the present invention is to provide a life nourishing and health protecting food product for conditioning blood stasis constitution.

In order to achieve the above object, according to one aspect of the present invention, there is provided a solid beverage for conditioning blood stasis constitution.

The solid beverage for conditioning blood stasis constitution according to the present invention comprises the following components in parts by weight: 21-55 parts of hawthorn, 9-33 parts of peach seed, 9-33 parts of gingko, 5-21 parts of *Platycodon grandiflorus,* 9-33 parts of dried tangerine peel, 0.5-4 parts of cinnamon, 9-33 parts of the root of kudzu vine, 2-21 parts of *Dahurian angelica,* 10-29 parts of dextrin, 7-25 parts of maltodextrin, 8-26 parts of soluble starch and 0.05-0.2 parts of aspartame.

Hawthorn is sour and sweet in flavor and slightly warm in nature; acts on spleen, stomach and liver; has the efficacies of promoting digestion and invigorating stomach, promoting the circulation of qi and dissipating blood stasis, and resolving turbidity and lowering lipid; and is used for meat-type food accumulation, abdominal fullness and distention, dysentery abdominal pain, blood stasis amenorrhea, puerperal blood stasis, heart and abdomen prickling, chest stuffiness and pains, colic pain, and hyperlipemia.

Peach seed is bittersweet in flavor and neutral in nature; acts on heart, liver and large intestine; has the efficacies of promoting blood circulation to remove blood stasis, loosening the bowels to relieve constipation, and relieving cough and asthma; and is used for amenorrhea and dysmenorrhea, lump in the abdomen, pulmonary abscess and intestinal carbuncle, injuries from falling down, constipation due to intestinal dryness, and cough and dyspnea.

Gingko is sweet, bitter and astringent in flavor and neutral in nature; is slightly toxic; acts on lung; has the efficacies of astringing the lung and relieving asthma, inducing astringency and checking vaginal discharge; and is used for asthma and cough with copious whitish viscid sputum, morbid leukorrhea, gonorrhea, enuresis and frequent urination.

Platycodon grandifloras is bitter and acrid in flavor and neutral in nature; acts on lung; has the efficacies of facilitating the flow of the lung-qi, relieving sore throat, eliminating phlegm, and apocenosis; and is used for cough with copious whitish viscid sputum, oppression in the chest, pharyngalgia and hoarseness, pulmonary abscess and pyemesis.

Dried tangerine peel is acrid and bitter in flavor and warm in nature; acts on lung and spleen; has the efficacies of regulating vital energy and relieving epigastric distention, and drying dampness and resolving phlegm; and is used for cough with copious whitish viscid sputum, dyspepsia and acute alcoholism, nausea and retching, and stuffy feeling in chest.

Cinnamon is acrid and sweet in flavor and extremely hot in nature; acts on kidney, spleen, heart, and liver; has the efficacies of tonifying fire and helping yang, guiding fire to origin, eliminating cold to stop pain, warming meridian vessels; and is used for impotence and uterine cold, chills and pain of the waist and the knees, kidney deficiency-induced asthma, deficient yang with upper manifestation, vertigo and congestion of the eyes, chills and pain of chest and abdomen, deficiency cold vomiting and diarrhoea, cold abdominal colic, dysmenorrhea and amenorrhea.

The root of kudzu vine is sweet and acrid in flavor and cold in nature; acts on lung and stomach; has the efficacies of relieving the muscles and skin and defervescence, promoting eruption, helping produce saliva and slaking thirst, and invigorating splenic yang for checking diarrhea; and is used for fever with superficies syndromes, strong pain in back, measles without adequate eruption, pyreticosis thirst, yin-deficiency consumptive thirst, heat diarrhea and heat-type dysentery, spleen deficiency diarrhea.

*Dahurian angelica* is acrid in flavor and warm in nature; acts on lung, spleen, stomach; has the efficacies of relieving exterior syndromes and dispelling pathogenic cold, dispelling wind and relieving pain, relieving stuffy nose, eliminating dampness and checking vaginal discharge, apocatastasis and apocenosis, and dispelling wind and arresting itching; and is used for common cold due to wind-cold, headache, toothache, arthralgia due to wind-dampness, nasosinusitis, morbid leukorrhea, and pyogenic infection with abscess.

The blood stasis constitution refers to the body constitution prone to sluggish circulation of the blood or incapability of dissipation of internal hemorrhage to cause internal stagnation of the blood, when internal organs are dysfunctional, which often has the manifestations of dark complexion, rough and brown skin, chromatosis possibly with purpura, pale lips, cyanotic tongue possibly with petechiae, and thready and uneven pulse. The blood stasis constitution has varied symptoms, and the general therapeutic principle is promoting blood circulation to dispel blood stasis. In this prescription, hawthorn promotes digestion, promotes the circulation of qi and dissipates blood stasis, peach seed promotes blood circulation to remove blood stasis, the dried tangerine peel regulates vital energy and relieves epigastric distention, and they jointly serve the function of promoting blood circulation to dispel blood stasis. *Platycodon grandifloras* facilitates the flow of the lung-qi and eliminates phlegm; gingko astringes the lung and induces astringency; cinnamon helps yang and eliminates cold; the root of kudzu vine can promote eruption and help produce saliva; and *Dahurian angelica* relieves exterior syndromes and dispels pathogenic cold. In the present invention, hawthorn, peach seed and dried tangerine peel are dominant (monarch) components, gingko, *Platycodon grandiflorus* and the root of kudzu vine are subordinate (ministerial) components, and cinnamon and *Dahurian angelica* are adjuvant (envoy) components. In addition, dextrin, maltodextrin and aspartame, on the one hand, can give play to medicinal effect and balance the nutritional ingredients, and on the other hand, can be used for flavoring.

Figure 1:
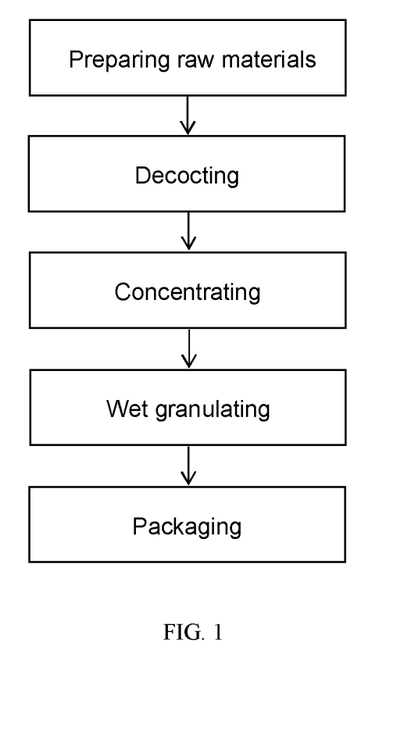
FIG. 1 is a production process of a solid beverage according to an embodiment of the present invention.

As shown in FIG. 1, the method for producing a solid beverage for conditioning blood stasis constitution comprises the steps of:

(1) preparation of raw materials: subjecting peach seed, hawthorn, the root of kudzu vine, gingko, dried tangerine peel, *Dahurian angelica, Platycodon grandiflorus* and cinnamon to impurity removal, cleansing, cutting and pulverization, and then mixing them for later use, wherein the proportion of each raw material provided in the present invention is used herein;

(2) decoction: decocting the mixture resulting from step (1) with water twice to obtain a traditional Chinese medicine liquid;

(3) concentration: pumping the traditional Chinese medicine liquid prepared in step (2) into an inspissator through a pipe to concentrate the same into thick paste;

(4) wet granulation: mixing and stirring dextrin, maltodextrin, soluble starch and aspartame to obtain a mixture adjuvant, adding the thick paste prepared in step (3) to the mixture adjuvant, and stirring the same for granulation; and (5) packaging: subjecting the product resulting from the wet granulation to the packaging step to obtain a finished product.

The purpose of step (1) is to remove fat from the seed medicinal materials, pulverize the resultant seed medicinal materials and pass them through a 2-mesh sieve; the rhizomatic medicinal materials contain cellulose, and are rich in starch, and cutting or pulverization extraction can effectively retain the target ingredients thereof, and prevent polysaccharide swelling; and cleansing can remove impurities and soil, and effectively reduce the residuals of pollutants such as heavy metals and pesticides.

The two-time decoction process in step (2) is carried out as follows: the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction.

The temperature for the concentration in step (3) is 70-80° C., and the relative density of the prepared thick paste is 1.2-1.5 at the temperature of 50° C. The low-temperature evaporation can effectively reduce the decomposition of thermosensitive components, such as citric acid, malic acid, oxalic acid and other organic acids, and leads to high concentration efficiency without discharge of solvent steam, which facilitates evaporation, and is pollution-free to the environment, as it is carried out in an airtight space.

Figure 2:
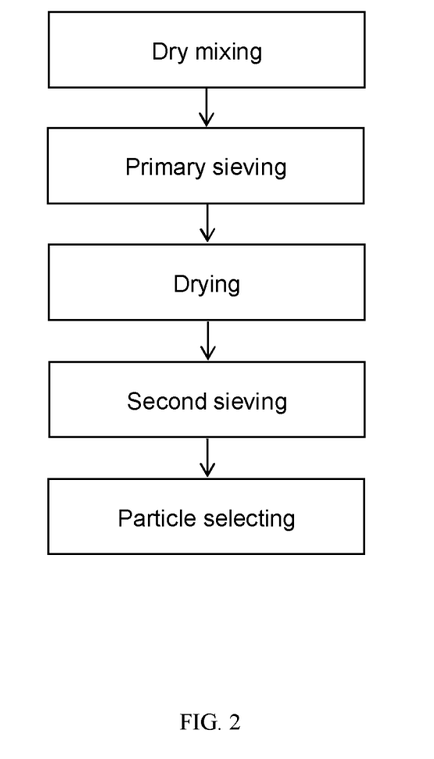
FIG. 2 is the specific steps of wet granulation in the production process of the solid beverage according to an embodiment of the present invention.

As shown in FIG. 2, the wet granulation in step (4) comprises the steps of:

(4.1) dry mixing: putting dextrin, maltodextrin, soluble starch and aspartame into an efficient mixer-granulator for mixing and stirring for 15 minutes to obtain a mixture adjuvant, wherein the proportion of each raw material provided in the present invention is used herein;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving, wherein stirring granulation can preferably prevent separation of the components, and since segregation phenomenon can easily occur due to the existence of differences in the particle size and density of the mixed extract components, granulation not only can effectively solve this problem, but also can remarkably improve the solubility;

(4.3) drying: putting the sieved particles prepared from step (4.2) into a boiling dryer for drying, wherein fluidized drying can effectively control the particle size distribution and control the product moisture; and (4.4) secondary sieving: carrying out secondary sieving by using a wig-wag machine, wherein by means of the secondary sieving, it is possible to control the particle distribution, bulk density and compactness.

In the above steps, the sieve for the primary sieving is a 12-mesh sieve, and the sieve for the secondary sieving is a 10-mesh sieve.

In the drying process in the above step (4.3), the temperature of the materials is controlled to be 70-80° C., and the moisture of the final materials is controlled to be 5% or less. In this step, pot turning can be frequently carried out according to the drying condition of the materials, so that the final material moisture meets the requirements.

On the basis of the implementation modes above, after the secondary sieving, the method further comprises a particle selecting step to select particles of 10-60 meshes. By means of particle selection, it is possible to improve the appearance and uniformity of the product particles. In practice, after the completion of the particle selection, it is feasible to make a record and tag the product to indicate the product name, the lot number, the specification, the net weight, the production date, the post name and the responsible person, fill in the equipment receipt, and transfer the product into an intermediate station.

Embodiment 1

The solid beverage for conditioning blood stasis constitution comprises the following components in parts by weight: 21 parts of hawthorn, 9 parts of peach seed, 9 parts of gingko, 5 parts of *Platycodon grandiflorus,* 9 parts of dried tangerine peel, 0.5 parts of cinnamon, 9 parts of the root of kudzu vine, 2 parts of *Dahurian angelica,* 10 parts of dextrin, 7 parts of maltodextrin, 8 parts of soluble starch and 0.05 parts of aspartame.

The production method thereof is as follows:

(1) preparation of raw materials: subjecting peach seed, hawthorn, the root of kudzu vine, gingko, dried tangerine peel, *Dahurian angelica, Platycodon grandiflorus* and cinnamon to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction;

(3) concentration: pumping the traditional Chinese medicine liquid prepared in step (2) into an inspissator through a pipe to concentrate the same into thick paste, wherein the temperature for the concentration is 70° C., and the relative density of the prepared thick paste is 1.2 at the temperature of 50° C.;

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve;

(4.3) drying: putting the sieved particles prepared from step (4.2) into a boiling dryer for drying, wherein the temperature of the materials is controlled to be 70° C., and the moisture of the final materials is controlled to be 5%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormity, the bagged particles are sealed and stored in a clean container, with the product name, the lot number, the number, the date and the like indicated for later use; the reference loading amount is 8 g per bag, and the loading limit is 8 g/bag±5%.

Embodiment 2

The solid beverage for conditioning blood stasis constitution comprises the following components in parts by weight: 55 parts of hawthorn, 33 parts of peach seed, 33 parts of gingko, 21 parts of *Platycodon grandiflorus*, 33 parts of dried tangerine peel, 4 parts of cinnamon, 33 parts of the root of kudzu vine, 21 parts of *dahurian angelica*, 29 parts of dextrin, 25 parts of maltodextrin, 26 parts of soluble starch and 0.2 parts of aspartame.

The production method thereof is as follows:

(1) preparation of raw materials: subjecting peach seed, hawthorn, the root of kudzu vine, gingko, dried tangerine peel, *Dahurian angelica, Platycodon grandiflorus* and cinnamon to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction;

(3) concentration: pumping the traditional Chinese medicine liquid prepared in step (2) into an inspissator through a pipe to concentrate the same into thick paste, wherein the temperature for the concentration is 80° C., and the relative density of the prepared thick paste is 1.5 at the temperature of 50° C.;

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve;

(4.3) drying: putting the sieved particles prepared from step (4.2) into a boiling dryer for drying, wherein the temperature of the materials is controlled to be 80° C., and the moisture of the final materials is controlled to be 3%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormity, the bagged particles are sealed and stored in a clean container, with the product name, the lot number, the number, the date and the like indicated for later use; the reference loading amount is 8 g per bag, and the loading limit is 8 g/bag±5%.

Embodiment 3

The solid beverage for conditioning blood stasis constitution comprises the following components in parts by weight: 30 parts of hawthorn, 15 parts of peach seed, 17 parts of gingko, 9 parts of *Platycodon grandiflorus*, 15 parts of dried tangerine peel, 1 part of cinnamon, 14 parts of the root of kudzu vine, 8 parts of *Dahurian angelica*, 19 parts of dextrin, 10 parts of maltodextrin, 13 parts of soluble starch and 0.1 parts of aspartame.

The production method thereof is as follows:

(1) preparation of raw materials: subjecting peach seed, hawthorn, the root of kudzu vine, gingko, dried tangerine peel, *Dahurian angelica, Platycodon grandiflorus* and cinnamon to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction;

(3) concentration: pumping the traditional Chinese medicine liquid prepared in step (2) into an inspissator through a pipe to concentrate the same into thick paste, wherein the temperature for the concentration is 75° C., and the relative density of the prepared thick paste is 1.45 at the temperature of 50° C.;

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve;

(4.3) drying: putting the sieved particles prepared from step (4.2) into a boiling dryer for drying, wherein the temperature of the materials is controlled to be 78° C., and the moisture of the final materials is controlled to be 3.4%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormity, the bagged particles are sealed and stored in a clean container, with the product name, the lot number, the number, the date and the like indicated for later use; the reference loading amount is 8 g per bag, and the loading limit is 8 g/bag±5%.

Embodiment 4

The solid beverage for conditioning blood stasis constitution comprises the following components in parts by weight: 30 parts of hawthorn, 15 parts of peach seed, 17 parts of gingko, 9 parts of *Platycodon grandiflorus,* 15 parts of dried tangerine peel, 1 part of cinnamon, 14 parts of the root of kudzu vine, 8 parts of *Dahurian angelica,* 19 parts of dextrin, 10 parts of maltodextrin, 13 parts of soluble starch and 0.1 parts of aspartame.

The production method thereof is as follows:

(1) preparation of raw materials: subjecting peach seed, hawthorn, the root of kudzu vine, gingko, dried tangerine peel, *Dahurian angelica, Platycodon grandiflorus* and cinnamon to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction;

(3) concentration: pumping the traditional Chinese medicine liquid prepared in step (2) into an inspissator through a pipe to concentrate the same into thick paste, wherein the temperature for the concentration is 73° C., and the relative density of the prepared thick paste is 1.33 at the temperature of 50° C.;

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve;

(4.3) drying: putting the sieved particles prepared from step (4.2) into a boiling dryer for drying, wherein the temperature of the materials is controlled to be 72° C., and the moisture of the final materials is controlled to be 4.5%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormity, the bagged particles are sealed and stored in a clean container, with the product name, the lot number, the number, the date and the like indicated for later use; the reference loading amount is 8 g per bag, and the loading limit is 8 g/bag±5%.

Embodiment 5

The solid beverage for conditioning blood stasis constitution comprises the following components in parts by weight: 40 parts of hawthorn, 20 parts of peach seed, 20 parts of gingko, 12 parts of *Platycodon grandiflorus,* 20 parts of dried tangerine peel, 2 parts of cinnamon, 20 parts of the root of kudzu vine, 12 parts of *dahurian angelica,* 19 parts of dextrin, 15 parts of maltodextrin, 15 parts of soluble starch and 0.1 parts of aspartame.

The production method thereof is as follows:

(1) preparation of raw materials: subjecting peach seed, hawthorn, the root of kudzu vine, gingko, dried tangerine peel, *Dahurian angelica, Platycodon grandiflorus* and cinnamon to impurity removal, cleansing, cutting and pulverization, and then mixing them for later use;

(2) decoction: decocting the mixture resulting from step (1) with water twice to obtain a traditional Chinese medicine liquid, wherein the two-time decoction process is carried out as follows:

the first decoction: adding water that is 10 times the weight of the mixture prepared in step (1), heating and boiling the resultant mixture, and pumping the liquid medicine into a stainless-steel liquid medicine storage tank through a pipeline filter immediately after boiling for 1.5 hours (starting from boiling); and the second decoction: adding water that is 8 times the weight of the mixture prepared in step (1), heating and boiling the resultant mixture, and pumping the liquid medicine into the stainless-steel liquid medicine storage tank through the pipeline filter immediately after boiling for 1.5 hours (starting from boiling) to evenly mix the liquid medicine with the liquid medicine obtained from the first decoction;

(3) concentration: pumping the traditional Chinese medicine liquid prepared in step (2) into an inspissator through a pipe to concentrate the same into thick paste, wherein the temperature for the concentration is 77° C., and the relative density of the prepared thick paste is 1.4 at the temperature of 50° C.;

(4) wet granulation (4.1) dry mixing: putting dextrin, maltodextrin, soluble starch and aspartame into an efficient mixer-granulator for mixing and stirring for 15 minutes to obtain a mixture adjuvant;

(4.2) primary sieving: adding batchwise the thick paste extracted from step (3) to the mixture adjuvant for mixing, stirring and granulation at the cutting speed I and the stirring speed I to obtain a soft material which is then subjected to primary sieving using a 12-mesh sieve;

(4.3) drying: putting the sieved particles prepared from step (4.2) into a boiling dryer for drying, wherein the temperature of the materials is controlled to be 76° C., and the moisture of the final materials is controlled to be 3.8%;

(4.4) secondary sieving: carrying out secondary sieving by using a wig-wag machine, using a 10-mesh sieve; and (4.5) particle selecting: selecting the particles of 10-60 meshes; and (5) packaging: bagging the particles, which have been mixed and have been tested to be qualified, by an automatic packaging machine according to standard operation procedures, wherein the appearance and the loading amount of the bag are timely detected, and corresponding measures are taken if there occurs any abnormity, the bagged particles are sealed and stored in a clean container, with the product name, the lot number, the number, the date and the like indicated for later use; the reference loading amount is 8 g per bag, and the loading limit is 8 g/bag±5%.

Experimental Example 1 the following is a test for the effects of the solid beverage for conditioning blood stasis constitution, which is prepared according to embodiment 5 of the present invention.

The basic conditions of the cases: 180 clinical cases of blood stasis constitution, including 90 male cases and 90 female cases. The youngest was aged 8, and the oldest was aged 77. 30 cases had chest pain and cough, anhelation, could not lie on the back due to dyspnea, suffered from chest stuffiness, palpitation, had dark purple tongue possibly with ecchymoses or petechiae; 30 cases had palpitation, cyanotic lips, cyanotic tongue possibly with ecchymoses or petechiae, unsmooth pulse or with drop beat; 30 cases had stomachache, and stomachache got worse when the stomach was pressed, the pain was aggravated after eating or the stomach had masses, stomachache was aggravated at night, even with the syndromes of hematochezia or haematemesis; 30 cases had painful swelling or bruises locally on the body, had purple tongue possibly with ecchymoses or petechiae; 30 cases had lesser abdominal pain, abnormal menstruation, dysmenorrhea, had purplish black menses with coagula, and had dark purple tongue possibly with ecchymoses; and 30 cases suffered from vertigo, prolonged headache, accompanied with the syndromes of amnesia, insomnia, palpitation, tinnitus and deafness, and had dark purple tongue possibly with ecchymoses.

The usage and dosage: the solid beverage was administered 8 g each time, twice a day; and was administered after being brewed with boiling water.

The evaluation criteria for therapeutic effects:

Being cured: the clinical symptoms were completely eliminated, and normal life was restored.

Being effective: the clinical symptoms were partially eliminated, and various signs were gradually improved.

Being ineffective: the symptoms and signs were not obviously improved.

Result statistics: 113 cases were cured, the solid beverage was effective to 46 cases and ineffective to 31 cases, i.e., the solid beverage was effective to 159 cases in total, therefore the total effective rate was 88.33%.

TABLE 1

Sensory Evaluation Scoring Criteria

| items | sensory evaluation | score |
|---|---|---|
| color | relatively dark | 1 |
| | intermediate | 5 |
| | relatively light | 1 |
| smell | strong smell of traditional Chinese medicine | 1 |
| | light smell of traditional Chinese medicine | 3 |
| | medicine fragrance | 5 |
| | relatively light | 3 |
| | light | 1 |
| taste | bitter and astringent | 1 |
| | relatively bitter | 3 |
| | fragrant and sweet | 5 |
| | relatively sweet | 3 |
| | excessively sweet | 1 |
| fineness and smoothness | fine and smooth | 5 |
| | having granular sensation | 3 |
| | having a throat-scratching feeling | 1 |
| | being hard to swallow | 0 |
| overall evaluation | poor | — |
| | ordinary | — |
| | good | — |

TABLE 2

Sensory Evaluation Results of Solid Beverages

| | items | control group | embodiment 1 | embodiment 2 | embodiment 3 | embodiment 4 | embodiment 5 | average |
|---|---|---|---|---|---|---|---|---|
| sensory evaluation (marks) | color | 43 | 93 | 96 | 92 | 95 | 97 | 94.8 |
| | smell | 24 | 95 | 95 | 97 | 97 | 94 | 92.4 |
| | taste | 58 | 90 | 97 | 95 | 96 | 96 | 95.8 |
| | fineness and smoothness | 88 | 91 | 93 | 92 | 92 | 93 | 93.2 |
| | average | 53.75 | 93.25 | 94.75 | 93.75 | 93.5 | 95 | 94.05 |
| over all evaluative (person-time) | good | 8 | 17 | 19 | 20 | 20 | 20 | 19.2 |
| | ordinary | 4 | 3 | 1 | 0 | 0 | 0 | 0.8 |
| | Poor | 8 | 0 | 0 | 0 | 0 | 0 | 0 |

Experimental Example 2: Sensory Evaluation

The solid beverages prepared in embodiments 1-5 were brewed with boiling water and used as experimental groups, and the mixed liquid medicine after two decoctions prepared in the process step (2) in embodiment 5 was used a control group, three replicates of samples were collected from each of the experimental groups and the control group, and were subjected to sensory evaluation by 20 professional sensory assessors. The sensory evaluation scoring criteria are shown in table 1, and the sensory evaluation results are shown in table 2.

As can be known from the above experimental results, the average scores on the aspects of color, smell, taste and fineness and smoothness of the solid beverages prepared in embodiments 1 to 5 as given by the 20 professional sensory assessors are all higher than the corresponding scores given for the control group. The results show that the solid beverage provided by the present invention is greatly improved in smell and taste, as compared with the liquid medicine obtained by decocting the traditional Chinese medicine decoction pieces, moreover, sweet flavor has been added thereto, the taste and the fine and smooth feeling are greatly improved, which makes the solid beverage provided by the present invention very suitable for everyday drinking.

Experimental Example 3: Animal Experiment

An animal experiment is conducted on blood stasis model rats using the solid beverages prepared in embodiments 1-5 to study the therapeutic effects of the solid beverage of the present invention on the experimental rats through control experiment.

(1) Hemorrheological Measurement:

The measurement method is as follows: after the rats were anesthetized, blood was drawn from the lower common carotids by means of catheterization, a multifunctional capillary viscometer was used to measure the whole blood viscosity $\eta b$ respectively at a high shear rate ($200\ s^{-1}$), a median shear rate ($30\ s^{-1}$) and a low shear rate ($5\ s^{-1}$), and an erythrocyte deformation/aggregation tester was used to measure the erythrocyte aggregation index RI.

(2) Creation of Acute Blood Stasis Rat Models

The SD rats in all the groups with the exception of the blank control group were administered with epinephrine Adr (0.8 mg/kg) by hypodermic injection, and then placed in an ice water bath for 4 minutes, 4 hours later, Adr was administered once again. 12 hours after the last injection, blood was drawn from the common carotids by means of catheterization, measurement is conducted to determine whether there is a significant difference between the model group and the blank control group in hemorrheological indexes $\eta b$ (high shear, median shear and low shear) and RI so as to determine whether is the creation of models was successful.

(3) Administration Mode

The blank control group (referred to as the blank group): saline (20 mL/kg) in a volume equal to that of the model group;

the acute blood stasis model group (referred to as the model group): saline (20 mL/kg); and the solid beverage experimental group (referred to as the experimental group): intragastrically administered with solid beverage particles at a dosage of 0.3 g/kg.

The experimental animals in each group were intragastrically administered twice a day, one in the morning and the other in the evening, 5 times in total, and 5 days later, blood was drawn from the common carotids of the rats in each group by means of catheterization, and hemorrheological indexes $\eta b$ (high shear, median shear and low shear) and the erythrocyte aggregation index RI of each group were measured.

(4) Test Results and Data Analysis (the Results being Shown in Table 3)

Compared with the blank group, both the whole blood viscosity (200, 30, $5\ s^{-1}$) and erythrocyte aggregation index in the model group were increased (P<0.01), which demonstrates that the creation of acute blood stasis models is successful.

Compared with the model group, all of the solid beverages prepared in the above embodiments 1-5 could reduce the whole blood viscosity and the erythrocyte aggregation index of the model rats.

(3) Embodiment 5 is superior to embodiments 1-4 in improving hemorrheology-related indexes ($\eta b$ and RI).

Thus, taking the results into account comprehensively, the solid beverage particles prepared by the present invention can obviously improve hemorrheology, and can be used for the improvement and conditioning of the blood stasis constitution.

TABLE 3

Detection Results of Whole Blood Viscosity and Erythrocyte Aggregation Index of Acute Blood Stasis Rat Models

| groups | $\eta b$ (mPa · s) | | | RI |
|---|---|---|---|---|
| | $200\ s^{-1}$ | $30\ s^{-1}$ | $5\ s^{-1}$ | |
| blank group | 3.62 ± 0.38 | 5.39 ± 0.57 | 9.36 ± 0.92 | 3.32 ± 0.44 |
| model group | 4.71 ± 0.61** | 6.77 ± 0.88** | 12.38 ± 1.35** | 3.99 ± 0.71* |
| embodiment 1 | 4.08 ± 0.45## | 6.53 ± 0.49## | 10.26 ± 1.08# | 3.74 ± 0.29## |
| embodiment 2 | 4.22 ± 0.52## | 6.09 ± 0.73## | 10.05 ± 0.94## | 3.86 ± 0.53# |
| embodiment 3 | 3.90 ± 0.37# | 5.55 ± 0.75## | 9.73 ± 0.76## | 3.55 ± 0.64## |
| embodiment 4 | 3.84 ± 0.40## | 5.43 ± 0.98## | 9.67 ± 0.79## | 3.43 ± 0.50## |
| embodiment 5 | 3.59 ± 0.55## | 5.33 ± 0.38## | 8.92 ± 0.85## | 3.30 ± 0.37## |

**P < 0.01 (compared with the blank group);
*P < 0.05 (compared with the blank group);
P < 0.01 (compared wtih the model group); and
P < 0.05 (compared with the model group)

The descriptions above are only preferred embodiments of the present invention, which are not used to limit the present invention. For a person skilled in the art, the present invention may have various changes and variations. Any modifications, equivalent substitutions, improvements etc. within the spirit and principle of the present invention shall all be included in the scope of protection of the present invention.

What is claimed is:

1. A solid beverage, characterized by comprising the following components in parts by weight: 21-55 parts of hawthorn, 9-33 parts of peach seed, 9-33 parts of gingko, 5-21 parts of *Platycodon grandiflorus*, 9-33 parts of dried tangerine peel, 0.5-4 parts of cinnamon, 9-33 parts of the root of kudzu vine, 2-21 parts of *Dahurian angelica*, 10-29 parts of dextrin, 7-25 parts of maltodextrin, 8-26 parts of soluble starch and 0.05-0.2 parts of aspartame.

2. The solid beverage according to claim 1, characterized by comprising the following components in parts by weight: 30-44 parts of hawthorn, 15-23 parts of peach seed, 17-28 parts of gingko, 9-17 parts of *Platycodon grandiflorus*, 15-28 parts of dried tangerine peel, 1-3 parts of cinnamon, 14-23 parts of the root of kudzu vine, 8-17 parts of *Dahurian angelica*, 19-24 parts of dextrin, 10-22 parts of maltodextrin, 13-22 parts of soluble starch and 0.1-0.15 parts of aspartame.

3. The solid beverage according to claim 1, characterized by comprising the following components in parts by weight: 40 parts of hawthorn, 20 parts of peach seed, 20 parts of gingko, 12 parts of *Platycodon grandiflorus*, 20 parts of dried tangerine peel, 2 parts of cinnamon, 20 parts of the root of kudzu vine, 12 parts of *Dahurian angelica*, 19 parts of dextrin, 15 parts of maltodextrin, 15 parts of soluble starch and 0.1 parts of aspartame.

4. A method for producing a solid beverage, characterized by comprising the steps of:
(1) preparation of raw materials: taking subjecting peach seed, hawthorn, the root of kudzu vine, gingko, dried tangerine peel, *Dahurian angelica*, *Platycodon grandiflorus* and cinnamon for cleansing, cutting and pulverization, and then mixing them for later use;
(2) decoction: decocting the mixture resulting from step (1) with water twice to obtain a liquid;

(3) concentration: pumping the liquid prepared in step (2) into an inspissator through a pipe to concentrate the same into thick paste; and (4) wet granulation: mixing and stirring dextrin, maltodextrin, soluble starch and aspartame to obtain a mixture adjuvant, adding the thick paste prepared in step (3) to the mixture adjuvant, and stirring the same for granulation.

5. The method for producing a solid beverage according to claim 4, characterized in that, the decocting the mixture resulting from step (1) with water twice to obtain a liquid in step (2) is carried out by the following processes of:

(a) adding water that is 10 times the weight of the mixture prepared in step (1), heating and boiling the resultant mixture, and pumping the liquid into a stainless-steel liquid storage tank through a pipeline filter immediately after boiling for 1.5 hours (starting from boiling); and (b) adding water that is 8 times the weight of the mixture prepared in step (1), heating and boiling the resultant mixture, and pumping the liquid into the stainless-steel liquid storage tank through the pipeline filter immediately after boiling for 1.5 hours (starting from boiling) to evenly mix the liquid with the liquid obtained from the process (a).

6. The method for producing a solid beverage according to claim 4, characterized in that, the temperature for the concentration in step (3) is 70-80° C., and the relative density of the prepared thick paste is 1.2-1.5 at the temperature of 50° C.

7. The method for producing a solid beverage according to claim 4, characterized in that, the wet granulation in step (4) comprises the steps of:

(4.1) dry mixing: putting dextrin, maltodextrin, soluble starch and aspartame into mixer-granulator for mixing and stirring for 15 minutes to obtain a mixture adjuvant;

(4.2) primary sieving: adding batchwise the thick paste extracted from step (3) to the mixture adjuvant for mixing, stirring and granulation in the mixer-granulator to obtain a soft material which is then subjected to primary sieving;

(4.3) drying: putting the sieved particles prepared from step (4.2) into a boiling dryer for drying; and (4.4) secondary sieving: carrying out secondary sieving by using an oscillating granulator machine.

8. The method for producing a solid beverage according to claim 7, characterized in that, the sieve for the primary sieving is a 12-mesh sieve, and the sieve for the secondary sieving is a 10-mesh sieve.

9. The method for producing a solid beverage according to claim 7, characterized in that, in the drying process in step (4.3), the temperature of the materials is controlled to be 70-80° C., and the moisture of the final materials is controlled to be 5% or less.

10. The method for producing a solid beverage according to claim 7, characterized in that, after the secondary sieving, the method further comprises a particle selecting step to select particles of 10-60 meshes.

* * * * *